United States Patent [19]

Weiland

[11] Patent Number: 5,070,881
[45] Date of Patent: Dec. 10, 1991

[54] ULTRASOUND APPARATUS FOR DETERMINING WHETHER A FEMALE LARGE ANIMAL IS GRAVID

[75] Inventor: Werner Weiland, Bendorf-Sayn, Fed. Rep. of Germany

[73] Assignee: Rheintechnik Weiland & Kaspar KG, Neunkirchen, Fed. Rep. of Germany

[21] Appl. No.: 478,696

[22] Filed: Feb. 12, 1990

[30] Foreign Application Priority Data

Feb. 23, 1989 [DE] Fed. Rep. of Germany ....... 3905567

[51] Int. Cl.$^5$ .............................................. A61B 8/00
[52] U.S. Cl. .............................................. 128/662.03
[58] Field of Search ...................... 128/660.10, 662.03, 128/662.04, 662.06

[56] References Cited

U.S. PATENT DOCUMENTS

| | | | |
|---|---|---|---|
| 4,080,960 | 3/1978 | Goans et al. | 128/661.03 |
| 4,112,927 | 9/1978 | Carlson | 128/661.03 |
| 4,333,474 | 6/1982 | Nigam | 128/660.01 |
| 4,671,289 | 6/1987 | Gainsley et al. | 128/661.03 |
| 4,869,260 | 9/1989 | Young et al. | 128/662.04 |
| 4,913,155 | 4/1990 | Dow et al. | 128/660.01 |

FOREIGN PATENT DOCUMENTS 2003701 3/1979 United Kingdom .......... 128/662.04

Primary Examiner—Francis Jaworski
Attorney, Agent, or Firm—Max Fogiel

[57] ABSTRACT

Ultrasound apparatus for determining whether a female large animal, especially a cow or a mare, is gravid, with an ultrasonic head (1) that has an ultrasound transmitter (7) and receiver (8) at one face (9) and with a housing (4) that accommodates a signal generator (28) and a battery (29) or a connection to an external source of electricity for operating the apparatus, whereby the transmitter-receiver is connected to the signal generator and battery or external-source connection by a cable, characterized in that a resilient annular structure (30) that projects beyond the face (9) of the ultrasonic head (1) and surrounds the transmitter (7) and receiver (8) is attached to the head in the vicinity of its face, and a handle (2 & 3) is connected to the outside of the ultrasonic head.

14 Claims, 1 Drawing Sheet

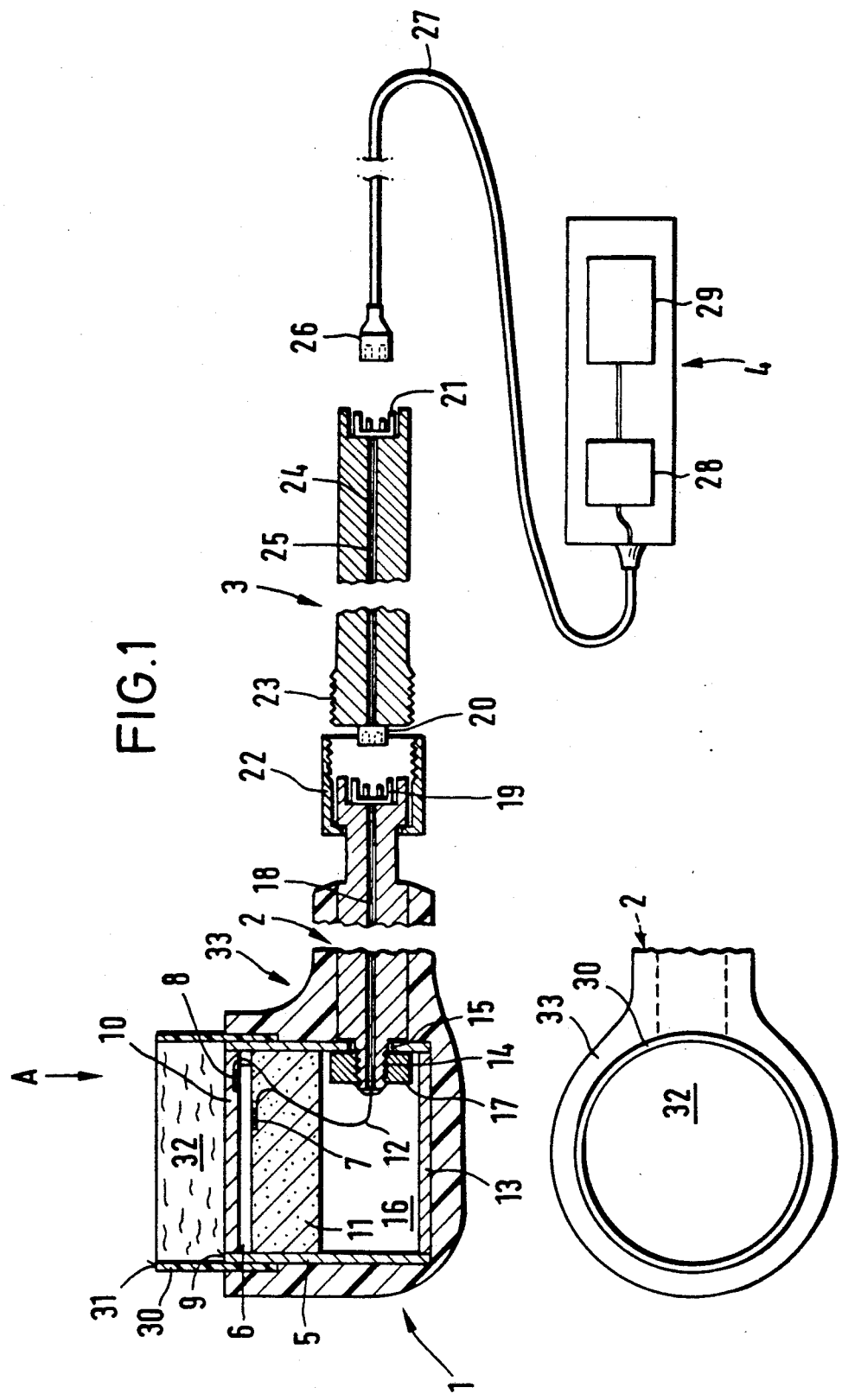

ULTRASOUND APPARATUS FOR DETERMINING WHETHER A FEMALE LARGE ANIMAL IS GRAVID

BACKGROUND OF THE INVENTION

The concerns ultrasound apparatus for determining whether a female large animal, especially a cow or a mare, is gravid, with an ultrasonic head that has an ultrasound transmitter and receiver at one face and with a housing that accommodates a signal generator and a battery or a connection to an external source of electricity for operating the apparatus, whereby the transmitter-receiver is connected to the signal generator and battery or external-source connection by a cable.

When detecting with ultrasound apparatus it is absolutely necessary in order to obtain informative results for the face of the ultrasonic head to rest flat against the subject being scanned, especially without any air gap between the face and the subject. A contacting agent, a gel or oil for example, is accordingly applied in practice to the face of the head.

Using ultrasound apparatus to determine whether a female large animal, especially a cow or mare, is gravid is particularly difficult because the animal will not hold still. It is accordingly not only necessary to pass the ultrasonic head over the animal's skin or hair while trying to locate the subject to be detected, entailing the risk of rubbing off the contacting agent, but the constant motion of the head makes it impossible to ensure reliable contact between it and the animal, without, that is, an air gap between them.

Ultrasound apparatus of this type is known from German GM 8 507 700 and is especially intended for use on swine, sheep, goats, and cows. The ultrasonic head has a rubber ring at the opposite end in the transmitter-receiver. The rubber ring is intended to prevent damage to the transmitter-receiver from the rough usage encountered in barns. One drawback to this known apparatus is that the ultrasonic head must be directly positioned by hand while the subject is being scanned and that there is nothing in the vicinity of the face of the ultrasonic head to prevent the contacting agent from being rubbed off while the head is being moved over the skin or hair of the animal. This apparatus can accordingly only be reliably employed in the barn once the animal being examined has been extensively immobilized and cannot thrash around and injure the person carrying out the examination. Using the apparatus outside, especially at remote locations where it is impossible to force the animal against the wall of the stall, however, is ruled out.

SUMMARY OF THE INVENTION

The object of the present invention is to provide apparatus of the aforesaid type that can be used to reliably determine whether a female large animal, especially a cow or mare and even one not in a stall, is gravid without the person carrying out the examination being injured by the animal being examined.

This object is attained in accordance with the invention in that a resilient annular structure that projects beyond the face of the ultrasonic head and surrounds the transmitter and receiver is attached to the head in the vicinity of its face, and a handle is connected to the outside of the ultrasonic head.

The ultrasonic head with a resilient annular structure in accordance with the invention ensures that the contacting agent applied to the face of the ultrasonic head toward the transmitter and receiver will remain inside the area surrounded by the annular structure while the ultrasonic head is being moved over the skin or hair of the animal. It will be obvious that it is practical to apply the contacting agent to the ultrasonic head thickly enough to ensure that its open area will share a plant with the upper surface of the annular structure. Although some contacting agent can, due to the resilience of the annular structure, leak out from between it and the animal's skin or hair while the ultrasonic head is being moved back and forth, still, only contacting agent will remain between the face of the ultrasonic head and the animal's skin or hair, eliminating any cushion of air to contaminate the results. The special seal between the ultrasonic head and the animal being examined that derives from the resilient annular structure makes it possible to take extensive irregularities in the ultrasonic head into account to the extent that a handle can be secured to the head, allowing it to be applied from farther away and providing the examining person with more safety. The examiner will in practice hold the free end of the handle, apply the contacting agent, the aforesaid gel or oil, for example, to the conveniently horizontal face of the ultrasonic head up to the upper surface of the resilient annular structure, and positioning the head against the animal being examined, with the annular structure sealing the contacting agent in. Although tilting the ultrasonic head will compress the annular structure on one side of the head more powerfully than on the other side, the structure will still prevent air from entering the area it surrounds, ensuring precise-scanning conditions even when the ultrasonic head must be moved back and forth over the animal's skin or hair. The invention is not restricted to embodiments wherein the ultrasonic head is a component separate from the handle, and both can be integrated into one part, a single casting for example.

The ultrasonic head in one preferred embodiment of the invention is a closed circular cylinder, to the outer surface of which and adjacent to the face, the resilient annular structure that projects beyond the face is attached. The cylinder embodiment simplifies the design of the ultrasonic head, which has an annular structure that is definitely circular in this case. The annular structure itself can be a flat rubber ring for example. The annular structure can be secured to the ultrasonic head in any desired way, although it is preferred for the annular structure to be cemented to the outer surface of the cylinder to provide a seal between the two components.

It is, however, not absolutely necessary for the annular structure to be attached to the outer surface of the cylinder. It is for example also possible to provide a groove around the face of the ultrasonic head with the annular structure fitting tight into it. It is also practical for the ultrasonic head and optionally the handle as well to have a protective coating of rubber or a similar material cast around it or them, which can also surround the resilient annular structure to some extent.

How far the annular structure projects above the face of the ultrasonic head or the protective coating around the head depends on the particular requirements, given that the contacting agent must be kept from rubbing off the head. When for example an animal has long hair in the area of the body that is to be examined, the annular structure must project farther than if the animal has short hair. In this sense the annular structure can project as much as 20 mm, although any farther projection is of subordinate significance in that the resilient annular structure will yield when the ultrasonic head is forced against the animal being examined, decreasing the extent it projects to, even in relation to the thickness of the hair.

To prevent the cable leading to the ultrasonic head from getting in the way during the examination, it can extend through the handle. It is also of advantage for the end of the handle remote from the ultrasonic head to contain a connector, especially a plug, for electrically attaching a section of the cable associated with the housing to another section associated with the ultrasonic head. Since it is also necessary for the ultrasonic head to extend over quite a distance to the animal being examined, it is considered of advantage for the end of the handle remote from the ultrasonic head to have two connectors, especially plugs, to allow mechanical and electric connection with an extension handle or with a section of cable extending through an extension handle.

BRIEF DESCRIPTION OF THE DRAWINGS

One but not the only embodiment of the invention will not be described in detail with reference to the drawing, wherein FIG. 1 is a longitudinal section through ultrasound apparatus in accordance with the invention and FIG. 2 is a view of the ultrasonic head on the apparatus in accordance with the invention in the direction A indicated in FIG. 1.

DESCRIPTION OF THE PREFERRED EMBODIMENTS

The ultrasound apparatus in accordance with the invention consists essentially of an ultrasonic head 1, of a handle 2 secured to it, of an extension 3 of the handle, and of equipment 4.

Specifically, ultrasonic head 1 consists of a circular cylinder 5 with a piezo-oxide disk 6 positioned at the top, in terms of FIG. 1, and at a distance from the top. On each side of the disk are the active components of an ultrasound transmitter 7 and an ultrasound receiver 8, and between piezo-oxide disk 6 and the free end of cylinder 5 is an intermediate 10 with an area equaling the open cross-section of the cylinder 5. The surface of intermediate 10 facing disk 6 fits tight inside cylinder 5. There is a filler 11 on the side of piezo-oxide disk 6 facing away from intermediate 10. An electric cable 12 that connects to ultrasound transmitter 7 and receiver 8 extends through filler 11. The bottom of cylinder 5 is closed off with a circular plate 13.

A narrower threaded section 14 of handle 2 extends through a bore 15 in the surface of cylinder 5 and into the space 16 between filler 11 and plate 13. Screwed onto threaded section 14 is a nut 17, tightly securing handle 2 to cylinder 5. Handle 2 has a central bore 18 extending through it longitudinally and accommodating electric cable 12. The end remote from threaded section 14 has a negative plug component 19 connected to cable 12. Extension 3 is, like handle 2, shaped like a rod, with one end having a positive plug component 20 that fits into the negative component on handle 2. The other end of extension 3 has another negative plug component 21. When handle 2 and extension 3 are connected, a union nut 22 that moves back and forth axially between two stops on handle 2 engages a threaded section 23 on extension 3. Although handle 2 and extension 3 have been drawn separated for purposes of illustration, they will naturally represent a single unit in practice.

Extension 3 also has a central bore 24 extending through it longitudinally and accommodating an electric cable 25 that connects plug components 20 and 21. A subassembly with the negative plug component 21 in extension 3 constitutes a positive plug component 26 that is connected by way of another electric cable 27 to equipment 4. The essential elements of equipment 4 are, as schematically illustrated in FIG. 1, an electric signal generator 28, an audio alarm for example, and a battery 29 that powers the apparatus. All these components are of course electrically connected to electric cable 27. The other essential components needed to operate conventional ultrasound apparatus can be accommodated in equipment 4. This equipment is illustrated highly simplified in FIG. 1. Both handle 2 and extension 3 are represented broken in order to suggest that handles and extensions of various lengths can be employed as needed.

The two figures are also intended to imply that the outer surface of cylinder 5 is provided at its free end 9 with a resilient annular structure 30 that projects above that end. This structure is a shallow and soft rubber ring that is cemented to cylinder 5 where it comes into contact with it. As will be evident from FIG. 1, the section of resilient annular structure 30 that projects beyond the free end 9 of cylinder 5 is slightly larger than the section cemented to the cylinder. It is, however, completely within the scope of the invention for the projection section to be smaller, depending on the application. A contacting agent 32, a gel for example, is introduced into the space between free end 9 and the free end 31 of resilient annular structure 30 and surrounded by that structure.

It will also be evident from the figures that ultrasonic head 1 and handle 2 are provided with a protective rubber coating 33 and that the coated area is shaped more or less like a tobacco pipe. Protective coating 33 covers resilient annular structure 30 up to the level of the free end 9 of cylinder 5.

An ultrasonic head 1 in accordance with the invention with a resilient annular structure 30 surrounding the contacting agent 32 and with a cylinder 5 secured to a handle 2 and extension 3 can be used to determine whether even females of animals that might constitute some danger to the examiner are gravid. Handle 2 and extension 3 make it possible to extend ultrasonic head 1 over wide distances, and resilient annular structure 30 prevents rubbing off the contacting agent when the head is moved over the animal's skin or hair, leaving a cushion of air between the ultrasonic head and the air to contaminate or prevent results.

I claim:

1. An ultrasound apparatus for determining whether a female large animal as a cow, mare, or the like, is gravid, comprising: an ultrasonic head having an ultrasound transmitter and receiver at one face of said head; a signal generator in a housing and connected to said transmitter and receiver; a source of electricity connected to said transmitter and receiver as well as said signal generator; a resilient annular member projecting beyond said face of said ultrasonic head and surrounding said transmitter and receiver, said resilient annular member being secured to said ultrasonic head at a location adjacent said face; and handle means connected to the outside of said ultrasonic head, said resilient annular member protecting a contact agent applied to said face from being removed while said ultrasonic head is moved over the animal's surface through movement of said handle means; said resilient annular member having a rim forming an air-tight seal when placed against the animal's surface, said contact agent remaining within a space formed by said resilient annular member and said animal's surface while said ultrasonic head is moved on said animal's surface to produce increased accuracy of measurement; said handle means having a spacing between said ultrasonic head and hand of a user for preventing injury to the user by the animal while moving said head on the animal's surface.

2. An ultrasound apparatus as defined in claim 1, wherein said ultrasonic head comprises a closed circular cylinder having an outer surface adjacent to said face for securing thereto said resilient annular member projecting beyond said face.

3. An ultrasound apparatus as defined in claim 2, wherein said resilient annular member is cemented to said outer surface of said cylinder.

4. An ultrasound apparatus as defined in claim 1, wherein said ultrasonic head has a side opposite to said face, said side having a base closing off said ultrasonic head.

5. An ultrasound apparatus as defined in claim 1, wherein said resilient annular member comprises a substantially shallow rubber ring.

6. An ultrasound apparatus as defined in claim 1, wherein said face of said ultrasonic head has a groove around said face, said resilient annular member being inserted into said groove.

7. An ultrasound apparatus as defined in claim 1, including an electrical cable extending through said handle means.

8. An ultrasound apparatus as defined in claim 7, wherein said electrical cable has one section leading to said housing, said electrical cable having another section leading to said ultrasonic head; and a plug connector located at an end of said handle means remote from said ultrasonic head for connecting said one section of said cable and said other section of said cable.

9. An ultrasound apparatus as defined in claim 7, including an extension on said handle means, said cable passing through said extension; and plug connectors for connection to said extension at an end of said handle means remote from said ultrasonic head, said plug connectors connecting to said cable passing through said extension.

10. An ultrasound apparatus as defined in claim 1, wherein said ultrasonic head is enclosed in a protective coating comprised of rubber.

11. An ultrasound apparatus as defined in claim 10, wherein said protective coating surrounds partly said resilient annular member.

12. An ultrasound apparatus as defined in claim 10, wherein said protective coating surrounds said handle means.

13. An ultrasound apparatus as defined in claim 1, wherein said ultrasonic head and said handle means are comprised of a one-piece integral unit.

14. An ultrasound apparatus for determining whether a female large animal as a cow, mare, or the like, is gravid, comprising: an ultrasonic head having an ultrasound transmitter and receiver at one face of said head,; a signal generator in a housing and connected to said transmitter and receiver; a source of electricity connected to said transmitter and receiver as well as said signal generator; a resilient annular member projecting beyond said face of said ultrasonic head and surrounding said transmitter and receiver, said resilient annular member being secured to said ultrasonic head at a location adjacent said face; and handle means connected to the outside of said ultrasonic head, said resilient annular member protecting a contact agent applied to said face from being removed while said ultrasonic head is moved over the animal's surface through movement of said handle means; said resilient annular member having a rim forming an air-tight seal when placed against the animal's surface, said contact agent remaining within a space formed by said resilient annular member and said animal's surface while said ultrasonic head is moved on said animal's surface to produce increased accuracy of measurement; said handle means having a spacing between said ultrasonic head and hand of a user for preventing injury to the user by the animal while moving said head on the animal's surface; said ultrasonic head comprising a closed circular cylinder having an outer surface adjacent to said face for securing said resilient annular member projecting beyond said face; said ultrasonic head having a side located opposite to said face, said side having a base closing off said ultrasonic head; said resilient annular member comprising a substantially shallow rubber ring; said resilient annular member being cemented to said outer surface of said cylinder; an electrical cable extending through said handle means and having one section leading to said housing, said cable having another section leading to said ultrasonic head; a plug connector at an end of said handle means remote from said ultrasonic head for connecting to said one section and said other section of said electrical cable; said ultrasonic head having a protective coating comprised of rubber, said protective coating surrounding partly said resilient annular member and said handle means.

* * * * *